US006680177B2

(12) United States Patent
Mize

(10) Patent No.: US 6,680,177 B2
(45) Date of Patent: Jan. 20, 2004

(54) LOW MOLECULAR WEIGHT HEPARIN ASSAY, SYSTEM AND REAGENT THEREFOR

(75) Inventor: Patrick D. Mize, Durham, NC (US)

(73) Assignee: Cardiovascular Diagnostics, Inc., Morrisville, NC (US)

( * ) Notice: Subject to any disclaimer, the term of this patent is extended or adjusted under 35 U.S.C. 154(b) by 124 days.

(21) Appl. No.: 10/004,791

(22) Filed: Dec. 7, 2001

(65) Prior Publication Data

US 2003/0124638 A1 Jul. 3, 2003

(51) Int. Cl.$^7$ .............................. C12Q 1/56; C12Q 1/00; C12M 1/00; G01N 33/53
(52) U.S. Cl. .............................. 435/13; 435/4; 435/975; 435/283.1
(58) Field of Search .............................. 435/13, 4, 975, 435/283.1

(56) References Cited

U.S. PATENT DOCUMENTS

| 4,849,340 A | 7/1989 | Oberhardt ..................... 435/13 |
| 5,110,727 A | 5/1992 | Oberhardt ..................... 435/13 |
| 5,350,676 A | 9/1994 | Oberhardt et al. ............. 435/13 |
| 5,601,991 A | 2/1997 | Oberhardt ................... 435/7.91 |
| 5,658,723 A | 8/1997 | Oberhardt ...................... 435/4 |
| 5,670,329 A | 9/1997 | Oberhardt ..................... 435/13 |
| 5,677,133 A | 10/1997 | Oberhardt ................... 435/7.1 |
| 6,165,795 A | 12/2000 | Mize et al. .................. 436/69 |
| 6,197,494 B1 | 3/2001 | Oberhardt ...................... 435/4 |
| 2003/0124638 A1 * | 7/2003 | Mize .......................... 435/13 |

FOREIGN PATENT DOCUMENTS

WO   WO 01/44493 A2   6/2001

OTHER PUBLICATIONS

J. Harenberg, et al., Magnetic Bead Protamine–Linked Microtiter Assay for Detection of Heparin using Iodinated Low–Molecular–Mass Heparin–Tyramine, Thrombosis Research, vol. 79, No. 2, pp. 207–216, 1995.

* cited by examiner

Primary Examiner—Louise N. Leary
(74) Attorney, Agent, or Firm—Oblon, Spivak, McClelland, Maier & Neustadt, P.C.

(57) ABSTRACT

A method, kit, system and reagent for measuring low molecular weight heparin in a whole blood sample is provided which involves the use of a Factor Xa activator, such as Russell's Viper Venom, as the coagulation assay initiator.

26 Claims, 6 Drawing Sheets

Fig. 5: Correlation of the Rapidpoint®Coag Enoxaparin Test to the STACHROM LMWH Test - Average of Duplicates

LOW MOLECULAR WEIGHT HEPARIN ASSAY, SYSTEM AND REAGENT THEREFOR

BACKGROUND OF THE INVENTION

1. Field of Invention

The present invention relates to a dry chemistry format assay for measuring the low molecular weight heparin content of a whole blood sample, and a system and reagent for performing such an assay.

2. Discussion of the Background

Low molecular weight heparins (LMWHs) are a heterogeneous group of antithrombotic drugs produced from unfractionated heparin (UFH) using diverse chemical and enzymatic processes. LMWHs, like UFH, exhibit an anticoagulant effect by complexing with antithrombin (AT) to inactivate several of the coagulation enzymes preventing fibrin formation. Of these, Factor Xa and thrombin (IIa) are the most responsive to inhibition. LMWHs, introduced as antithrombotic drugs in the mid-1980s, are now established as the drug of choice for surgical thromboprophylaxis and are increasingly replacing UFH in the acute treatment of venous thromboembolic disorders. The low molecular weight heparin, enoxaparin, increasingly is used in patients with unstable angina (UA) and non-Q-wave myocardial infarction (NQMI) (J. Fareed et al, Past, present and future considerations on low molecular weight heparin differentiation: an epilogue. Semin Thromb Hemost, 25 Suppl 3:145–7 (1999), and J. Hirsh et al, Heparin and low-molecular-weight heparin: mechanisms of action, pharmacokinetics, dosing, monitoring, efficacy, and safety. Chest, January; 119(1 Suppl):64S–94S (2001)), who transition to percutaneous coronary intervention (PCI) (Lovenox (enoxaparin sodium) injection package insert, ©1998, rev. January, 2001). Although the activated partial thromboplastin time (aPTT) and activated clotting time (ACT) are the most common methods used to monitor UFH, they are relatively insensitive to LMWHs, such as enoxaparin. While chromogenic anti-Xa assays are commonly used to monitor the concentration of LMWHs, such assays provide an indirect measure of drug concentration and results are not routinely available in a cardiac catheterization laboratory setting.

The LMWHs have mean molecular weights between 4000 to 6000 daltons, and they have less ability to inactivate thrombin compared to UFH. Each LMWH is a specific mixture often demonstrating a unique anti-Xa/anti-IIa ratio and signature anticoagulant profile. The result is an anti-Xa/anti-IIa ratio of approximately 3 to 14:1 (depending on the brand of LMWH, dosage, and route of administration) compared to the 1:1 ratio observed with UFH$^{(Lovenox\ P.I.)}$. The LMWH, enoxaparin, has a mean molecular weight of approximately 4,500 daltons and, given at a dose of 1.5 mg/kg subcutaneously (SC), is characterized by a higher ratio of anti-Factor Xa to anti-Factor IIa activity (mean±SD, 14.0±3.1) (based on areas under anti-Factor activity versus time curves) compared to the ratios observed for heparin (mean±SD, 1.22±0.13)$^{(Lovenox\ P.I.)}$. This is an important distinction because the ability to prolong the aPTT and ACT is proportional to anti-IIa activity. Chromogenic anti-Xa assays provide estimates of enoxaparin concentration only in dilute, supplemented plasma and are not suitable for point-of-care (POC) testing.

More recently, clinical trials have confirmed the safety and efficacy of the LMWH, enoxaparin sodium (Lovenox®, Clexane®), in the management of acute coronary syndromes (ACS) (J. Fareed et al., Thromosis and Hemostasis, Supplement 3, Vol. 25, 3–4 (1999)).

Blood clotting reactions, in general, are employed as clinical assays to measure the time required for the formation of a fibrin clot. Blood clotting assays are principally used for screening, diagnosis, and for monitoring patients receiving anticoagulant therapy. There are many types of coagulation assays. These include prothrombin time (PT), partial thromboplastin time (PTT), activated partial thromboplastin time (APTT), fibrinogen assay, thrombin clotting time (TCT), activated clotting time (ACT), etc.

Before performing conventional clotting tests, a blood sample is collected in a tube or syringe containing anticoagulant (citrate). The blood sample is centrifuged, and the plasma separated (e.g., by decantation) from the red blood cells. A measured quantity (usually 0.1 ml) of plasma is pipetted into the reaction vessel or cuvette. A measured amount of reagent is then added manually via pipette or automatically by means of other volumetric delivery systems capable of metering a known, preset quantity of reagent. Alternatively, the sample can be added to the reagent directly.

Typically, 0.2 ml of reagent is employed. The addition of the reagent initiates the reaction. Many existing blood clotting assays suffer from at least one of the following disadvantages: difficulty in performance, requirement of highly trained personnel, inaccuracy in measurement, reagent instability, large consumption of reagent, etc.

One solution to this problem was addressed in Oberhardt, U.S. Pat. No. 5,110,727, in which a dry reagent based reaction slide is provided for performing coagulation assays quickly, accurately and simply. Such tests are marketed by Pharmanetics, Inc.

The capacity of blood to clot, as well as to not clot, is dependent on a large number of enzymatic factors and cofactors. The ability of central clinical laboratories to reliably and conveniently assay for LMWH in whole blood or plasma samples can be critical in monitoring individuals in LMWH therapy. The blood coagulation system is dominated by sequential proteolytic activation reactions of inactive precursors, called zymogens. Forward clotting reactions are controlled by simultaneous activation of anticoagulant zymogens that serve to limit the extent of clot formation and initiate the fibrinolytic system to resolve the clot.

There is thus a strongly felt need for a simple, facile and accurate method for the performance of blood clotting assays, e.g., in medical applications. Such a method should be based on a minimum number of manipulations of either a sample or reagent. Ideally such a method should be easily utilized by persons without extensive clinical laboratory training and should require no sample or reagent-containing solution preparation. It should not suffer the problems associated with reagent instability and be very accurate. It should permit effective mixing of sample and reagent. It should require only a very small amount of sample. And it should be able to perform automatic treatments of the sample, e.g., it should not require centrifugation of the blood sample or any other off line cell separation process. Available clotting parameter assays likewise suffer salient disadvantages.

Since the tests currently used for LMWHs are chromogenic assays requiring isolation of derived plasma from whole blood samples and significant processing time for performing the assay, an assay is needed that can quantitatively measure LMWHs quickly and easily, using whole blood and be performed at the bedside, in order to provide rapid determinations of LMWH therapeutic levels.

Additionally, conventional chromogenic assays measure actual levels of LMWH in the plasma sample, but do not reflect the actual clotting dynamics of the patient's blood. Since the clotting dynamics can depend or be confounded by a variety of factors, a test is needed that will correlate the clotting time with the amount of LMWH in the sample, and will also detect other possible problems in the clotting dynamics that are independent of the LMWH.

Clotting parameter assays are referred to herein as function and structure-based assays in the broad realm of coagulation diagnostics which do not utilize clot formation or clot lysis processes to generate end points. Most of these assays utilize chromogenic synthetic substrates to quantify molecular markers or specific factors or components associated with coagulation. These are typically functional reaction based assays as opposed to most immunoassays which could detect the same molecules but utilize structure recognition and may therefore still identify inhibited components or defective components, neither of which may be functional.

SUMMARY OF THE INVENTION

Accordingly, one object of the present invention is to provide an improved coagulation assay for LMWHs, particularly enoxaparin.

A further object of the present invention is to provide such an assay that can be performed using whole blood.

A further object of the present invention is to provide such an assay that is based on a dry chemistry format.

A further object of the present invention is to provide reagents for coagulation assays for measurement of LMWHs.

A further object of the present invention is to provide a coagulation based assay in dry chemistry format that relates clotting time to LMWH levels in a whole blood sample, while remaining sensitive to factors that can affect clotting time of the sample.

These and other objects of the present invention have been satisfied by the discovery of assays, reagents, methods and kits for measuring low molecular weight heparin concentration in a whole blood sample using a coagulation cascade reaction and monitoring coagulation times or kinetics, wherein the coagulation reagent is a dry format reagent comprising magnetic particles and a Factor Xa activator, such as Russell's Viper Venom.

BRIEF DESCRIPTION OF THE DRAWINGS

Many attendant features of this invention will become readily appreciated as the same becomes better understood by reference to the following detailed description when considered in connection with the accompanying drawings.

DETAILED DESCRIPTION OF THE PREFERRED EMBODIMENTS

Figure 1:
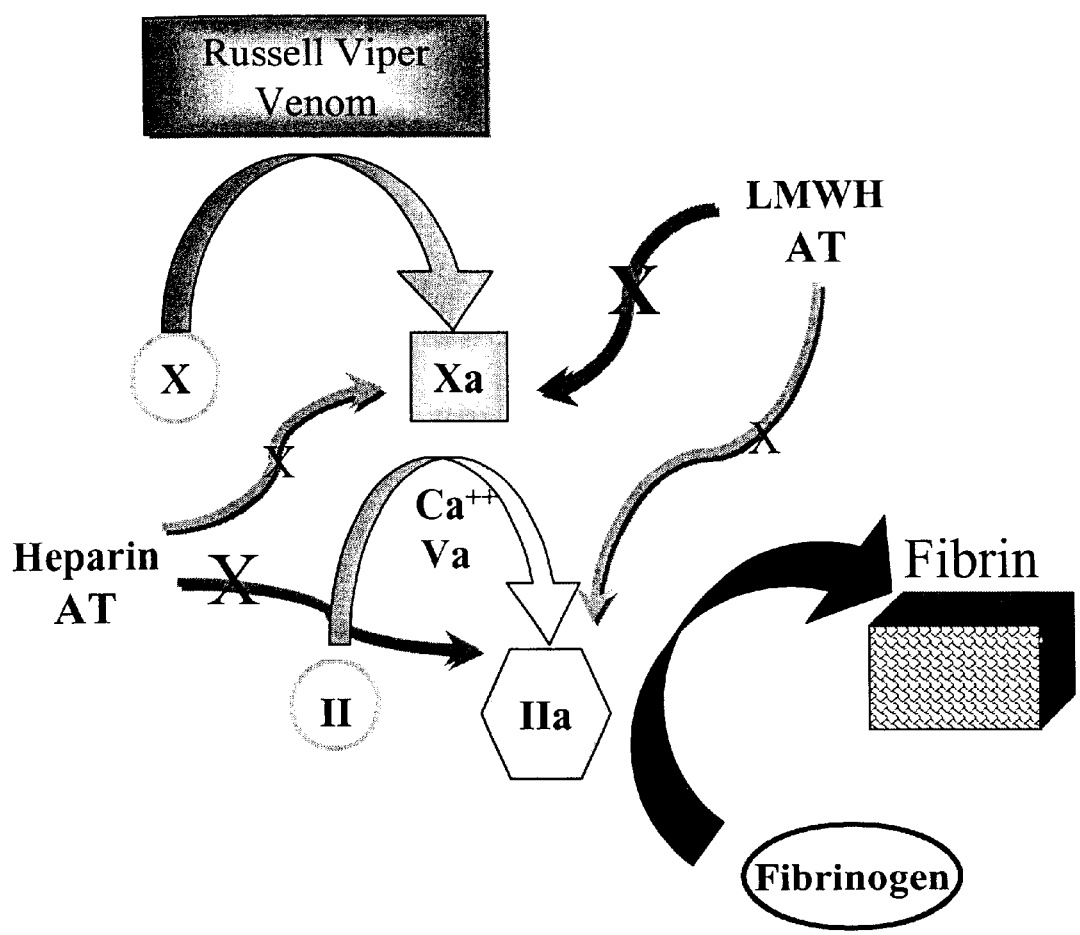
FIG. 1 provides a graphical depiction of the relevant portion of the coagulation cascade in blood.

The present invention relates to a method for measuring low molecular weight heparin concentration in a whole blood sample, comprising:

(i) combining a first, whole blood, component of the assay with a second component of the assay, wherein the second component comprises a dry coagulation assay reagent arranged in a substantially flattened configuration and containing magnetic particles distributed substantially homogeneously therethrough and comprising a factor Xa activator, and wherein the resulting mixture is subjected to (ia) an oscillating magnetic field or (ib) a moving permanent magnetic field or (ic) a combination of an oscillating magnetic field and a stationary permanent magnetic field or (id) a rotating magnetic field, whereby the combining of the first component with the second component substantially simultaneously initiates movement of the magnetic particles and a coagulation assay measurement; and (ii) monitoring movement induced in the magnetic particles by (ia) or (ib) or (ic) or (id) to obtain the coagulation assay measurement, wherein the coagulation assay measurement correlates to a concentration of low molecular weight heparin in the whole blood sample.

In the method of the present invention, the method is carried out in an element for performing the method, wherein the element comprises a channel structure defining a sample well and a reaction volume in fluid communication with each other, the reaction volume preferably containing the second component. The channel structure preferably has a geometry causing the first, whole blood, component placed in the sample well to be drawn into and fill the reaction volume via capillary action, wherein, after the reaction volume is filled, the first, whole blood, component (now combined with the second component and forming a resulting reaction mixture) remains stationary therein.

The element further preferably a means for channeling light from an outside source to the reaction volume, such as those described in the Pharmanetics patents. The method of the present invention further comprises using a means for detecting light scattered or absorbed or reflected from the reaction volume to monitor the reaction. Suitable means for detecting light are described in the Pharmanetics patents. Preferably, the reaction element is disposed in sufficiently close proximity to a permanent magnet and to an electromagnet such that the permanent magnet and the electromagnet provide a combination of an oscillating magnetic field and a stationary permanent magnetic field. More preferably, the element is situated between the permanent magnet and the electromagnet.

The present invention further relates to a method for measuring low molecular weight heparin concentration in a whole blood sample, comprising:

(i) adding a whole blood sample to a sample well of an element comprising:

a channel structure defining the sample well and a reaction volume in fluid communication with each other, wherein the reaction volume is defined by an upper surface having attached thereto a reflectance layer, comprising a semipermeable matrix wherein the reaction volume contains a measured amount of at least one dry coagulation assay reagent arranged in a substantially flattened configuration and containing magnetic particles distributed substantially homogeneously therethrough, wherein a specific volume of the sample is drawn into the reaction volume by capillary action and contacts, together with the semipermeable layer, the reagent to thereby substantially simultaneously initiate a coagulation assay measurement; and (ii) performing the coagulation assay measurement by measurement the reflectance of the semipermeable layer, wherein the dry coagulation assay reagent comprises a Factor Xa activator.

The present invention further relates to a kit for measuring low molecular weight heparin concentration in a whole blood sample, comprising, in one or more containers, a permanent magnet, a timing means, and an element containing at least one dry coagulation assay reagent arranged in a substantially flattened format and containing magnetic particles distributed substantially homogeneously therethrough, wherein the at least one dry coagulation assay reagent comprises a Factor Xa activator.

Additionally, the present invention relates to a system for measuring low molecular weight heparin concentration on a whole blood sample, comprising:

(i) an instrument with a means for temperature control, a means for producing an oscillating magnetic field or for moving a permanent magnetic field, an illuminating means, and a photometric monitoring means; and (ii) an element for performing the measuring, the element comprising a channel structure defining a sample well and reaction volume in fluid communication with each other, the channel structure having a geometry causing a liquid sample placed in the sample well to be drawn into and filling the reaction volume via capillary action, the reaction volume comprising at least one dry coagulation assay reagent arranged in a substantially flattened configuration and containing magnetic particles distributed substantially homogeneously therethrough, wherein the at least one dry coagulation assay reagent comprises a Factor Xa activator.

The system of the present invention can further comprise a transfer pipette, preferably made of an essentially nonthrombogenic material, and comprising a vented end. The transfer pipette is preferably capable of being filled with a liquid sample by capillary action, and is capable of expelling the liquid sample by means of pressure after covering or sealing the vented end. The instrument of the system further can comprise a heating means comprising a resistive heater strip and a thermistor situated in close proximity to the element. In the system of the present invention, the element is preferably suitable for performing a whole blood coagulation assay, with the channel structure having a geometry causing a blood sample placed in the sample well to be drawn into and filling the reaction volume via capillary action, wherein after the reaction volume is filled, the blood sample remains stationary therein, and wherein the element further comprises an optically or magnetically encodable information means, or both, capable of providing at least one of calibration, quality control, test parameter and patient information. The illuminating means of the system preferably includes one or more light sources to illuminate the element. The photometric monitoring means preferably comprises one or more detectors for photometrically monitoring chromogenic or chromomodulating species present in the reaction volume. Suitable means for the physical devices of the system of the present invention are described in the Pharmanetics patents.

The present invention further preferably relates to a system for measuring low molecular weight heparin concentration in a whole blood sample, comprising:

(i) a reaction element comprising (1) a sample well for receiving a liquid sample and (2) a reaction chamber containing a dry coagulation assay reagent arranged in a substantially flattened configuration and in which is embedded, substantially homogeneously therethrough, magnetic particles;

(ii) the sample well and reaction chamber being in fluid communication through a transport zone of geometry such that a volume of liquid sample placed in the sample well and corresponding to the volume of the reaction chamber is transported from the sample well to the reaction chamber simultaneously;

(iii) means for optically monitoring the reaction chamber;

(iv) means for subjecting the reaction chamber to an oscillating magnetic field;

(v) whereby, when the sample is introduced into the reaction chamber, the dry coagulation assay reagent is solubilized and the magnetic particles are thereby freed to move in an oscillating pattern induced by the oscillating magnetic field, thus providing a measurement of the kinetics of the coagulation assay corresponding to changes in the degree of the magnetic particles movement relative to the oscillating magnetic field, wherein the dry coagulation assay reagent comprises a Factor Xa activator.

The system preferably further comprises a means for controlling the moment transport of the liquid sample from the sample well to the reaction chamber is initiated. Suitable such means are described in the Pharmanetics patents. The system of the present invention can further comprise a plurality of reaction chambers in fluid communication with the sample well, and means for transporting a whole blood or plasma sample from one of the plurality of reaction chambers to another of the plurality of reaction chambers. In such an arrangement, it is possible to have the patient sample be split among the plurality of reaction chambers, with each reaction chamber having different coagulation reagents present for monitoring different aspects of the patients blood. Suitable such plural reaction chamber elements are likewise described in the Pharmanetics patents.

The present invention further relates to a method for measuring low molecular weight heparin concentration in a whole blood sample, comprising:

(i) subjecting to an oscillating magnetic field a reaction element bearing (1) a sample well for receiving a whole blood sample and (2) a reaction chamber containing a dry coagulation assay reagent arranged in a substantially flattened format and in which is embedded, substantially homogeneously therethrough, magnetic particles, the sample well and reaction chamber being in fluid communication through a transport zone of geometry such that a volume of sample placed in the sample well and corresponding to the volume of the reaction chamber is transported from the sample well to the reaction chamber simultaneously;

(ii) adding the whole blood sample susceptible to coagulation to the sample well whereby at least a part of the sample is introduced simultaneously to the reaction chamber, the reagent is solubilized and the particles are freed to move in an oscillating pattern induced by the oscillating magnetic field; and (iii) optically monitoring the reaction chamber to measure kinetics for the coagulation assay corresponding to changes in the degree of the particle movement relative to the magnetic field, wherein the dry coagulation assay reagent comprises a Factor Xa activator.

The present invention relates to an assay for a LMWH, in particular for enoxaparin (ENOX), in a whole blood sample using a dry chemistry format reagent. Preferable assay elements (such as test cards) and their methods of preparation are described in U.S. Pat. Nos. 4,849,340; 5,110,727; 5,350,676; 5,508,521; 5,601,991; 5,658,723; 5,670,329; 5,677,133; 6,165,795; and 6,197,494, the entire contents of which are hereby incorporated by reference (hereafter referred to as the "Pharmanetics patents"). However, the assay can be performed using assay elements of other types, as described below.

The present invention assay is designed to provide rapid results of the anticoagulant effect provided by LMWH, preferably enoxaparin sodium (Lovenox®, Clexane®). It is a one-step coagulation method performed on the Rapidpoint Coag analyzer, available from Bayer Corp. or on the TAS analyzer, available from Pharmanetics, Inc. The test utilizes citrated or non-citrated whole blood. Like other test devices described in the Pharmanetics patents, the LMWH test is a dry chemistry test card. All of the components necessary to perform the test, with the exception of the patient sample, are included within the reaction chamber of the card.

In the assay of the present invention, factor X is rapidly converted to factor Xa by the reagent containing a factor Xa activator, such as Russells' viper venom (RVV-X), initiating the clotting process, see FIG. 1. The assay element, preferably a test card as described in the Pharmanetics patents, contains the Factor Xa activator, but all clotting factors necessary for test function (Factor X and V, prothrombin, fibrinogen, and antithrombin) are supplied by the patient's sample. The assay measures the combined anti-Xa and anti-IIa activity of the low molecular weight heparin and is designed to measure clot times in citrated whole blood (CWB) over a broad range of comparable spiked-CWB derived plasma activities. Conventional tests for LMWH are only applicable up to about a range of anti-Xa activities from 0.0 to 1.0 anti-Xa IU/ml. However, the present assay provides the combined anti-Xa and anti-IIa activity of the LMWH and measures clot times in CWB comparable to a spiked-CWB derived plasma with an anti-Xa range of 0.0 to 3.0 anti-Xa IU/ml LMWH. The results generated by the present assay are indicative of the overall anticoagulant effect produced by the LMWH in whole blood.

The reagent comprises magnetic particles and a factor Xa activator. Suitable factor Xa activators include various Xa activating enzymes derived from snake venoms, including but not limited to Russell's Viper Venom (RVV-X), Vipera aspis aspis, Bothrops atrox, Saw-scaled viper Echis carinatus venom, and Cerastes cerastes venom.

The LMWH assay reagent of the present invention may further comprise one or more members selected from the group consisting of buffers, lyophilization aids, non-ionic detergents and proteins. Suitable buffers include, but are not limited to, HEPES, TRIS, and PIPES in the pH range of from 6.0 to 8.0, more preferably from pH 6.0–7.0, most preferably from pH 6.3–6.8. Preferred lyophilization aids include, but are not limited to, sucrose, lactose, mannitol and trehalose, with trehalose being most preferred. Non-ionic detergents are preferably one or more polysiloxanes combined with one or more detergents selected from Pluronic® surfactants, and PEO/PPO block copolymers. These components are preferably used in a combination of 1-10 wt % polysiloxane and 90–99 wt % of the Pluronic® or PEO/PPO block copolymer, most preferably in a 1:99 ratio of polysiloxane: Pluronic® or PEO/PPO block copolymer. The polysiloxanes used therein can be any polysiloxane type detergent, preferably polydimethylsiloxane PDMS detergents. The proteins useful in the present reagent preferably include, but are not limited to bovine serum albumin (BSA) and ovalbumin, with BSA being most preferred.

In the present assay, factor X is rapidly converted to factor Xa by the factor Xa activator, initiating the clotting process. The LMWH, preferably enoxaparin, from the patient's blood, complexes with antithrombin, to inhibit factor Xa and lengthen the clotting time in a dose-dependent manner. The reported clotting time increases in a dose dependent manner to the LMWH concentration present in the sample. The results generated by the test are indicative of the anticoagulant effect produced by the LMWH in whole blood.

Additionally, the results of the present assay can be used to determine if a patient is responding normally to LMWH therapy. For example, in certain patients, the blood is lacking in antithrombin, an essential factor needed for the anticoagulant effect of UFH or LMWH to work. When such a patient is monitored using conventional chromogenic LMWH assays, the assay returns only the level of LMWH, without reflecting the clotting dynamics of the patient's coagulation system. However, with the test of the present invention, one obtains a clotting time measurement that will readily show the physician that the level of LMWH is having little or no effect on the patient, since their clotting time will be relatively unchanged upon addition of increasing levels of LMWH. This will quickly tell the physician that there is another issue at play in the patient's anticoagulation status, thereby saving precious time in modifying the therapy. Using the conventional chromogenic tests, such results would require two or more tests to obtain and could easily be missed.

The test card of the present invention can be used to monitor the effects of the low molecular weight heparin (LMWH), preferably of Lovenox®/Clexane® (enoxaparin, sodium), in citrated or non-citrated whole blood.

The test provides information on patient's whole blood response to LMWH, such as enoxaparin by measurement of the clotting time using a factor Xa activated clotting method. To the present inventors' knowledge, the present assay provides the first assay for LMWHU that can be accurately performed using whole blood.

In the present invention, the magnetic particles are induced to move by being subjected to either (1) an oscillating magnetic field or (2) a moving permanent magnetic field or (3) a combination of an oscillating magnetic field and a stationary permanent magnetic field, or (4) a rotating magnetic field. The movement of the magnetic particles is then monitored in the performance of the assay. The magnetic field of the present invention can be generated using any of the magnetic field generating means described in the Pharmanetics patents. The movement of the magnetic particles is preferably detected and analyzed also as described in the Pharmanetics patents.

The clotting assays of this invention are performed on a reaction element. This reaction element can be any element which will support the reagents used in the assay and permit monitoring movement of the magnetic particles. Such reaction elements include microtiter plates, their equivalents, substantially flat surfaces or the reaction slide provided by the Pharmanetics patents.

The magnetic particles of the present invention assays are present in an amount of 0.5, or lower, to 50 milligrams of magnetic particles, preferably 1 to 10 milligrams, per milliliter of dry reagent.

Examples of this invention are set forth below. However, it is to be understood that these examples are given by way of illustration only and are not to be construed as limiting the invention either in spirit or in scope, as many modifications both in doses and methods could be possible to those skilled in the art.

EXAMPLES

Dose Response for Enoxaparin Embodiment of Present Assay

Figure 2:
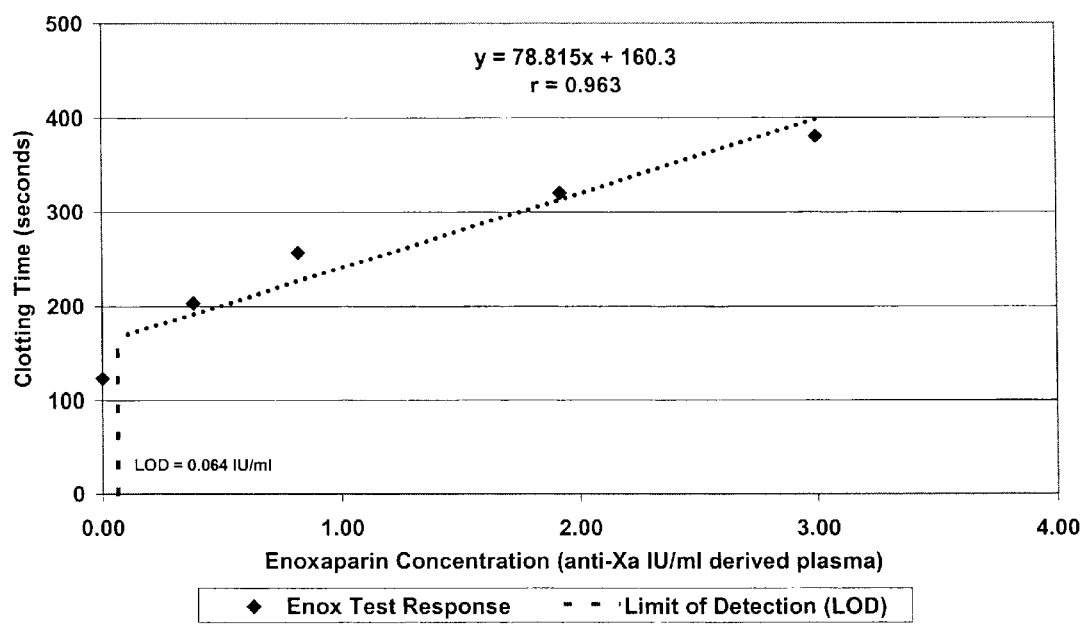
FIG. 2 provides a graphical representation of the in vitro clotting time response of citrated whole blood at different levels of the preferred LMWH enoxaparin.
Figure 3:
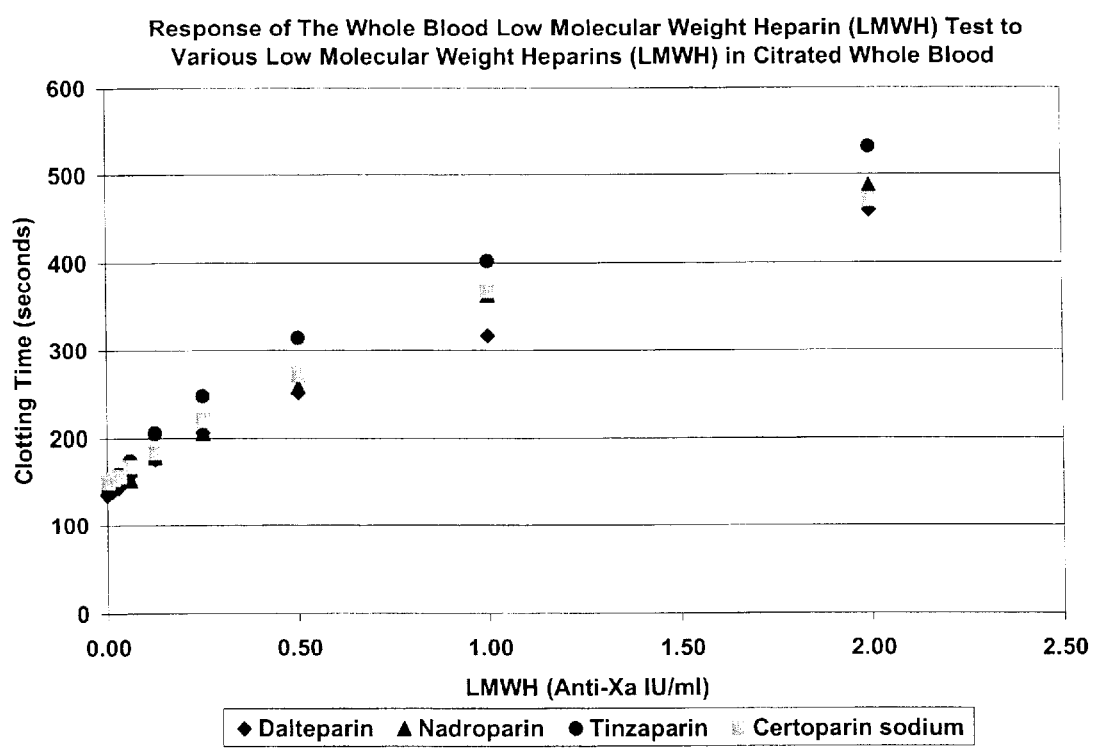
FIG. 3 provides a graphical representation of in vitro clotting time response of citrated whole blood at varying levels of four other LMWHs.

An in vitro dose-response relationship between mean ENOX CWB clotting times for 10 individuals and the derived plasma enoxaparin concentrations is shown in FIG. 2 and TABLE 1.

TABLE 1

Combined In Vitro Response of Rapidpoint ® Coag ENOX
Test to Enoxaparin in CWB from 10 Individual Donors

| Mean Anti-Xa* | 0.0 | 0.38 | 0.82 | 1.92 | 3.0 |
|---|---|---|---|---|---|
| Mean C.T. | 122.8 | 203.1 | 256.8 | 320.7 | 380.7 |
| SD | 21.1 | 24.9 | 27.3 | 34.7 | 40.2 |

*Anti-Xa measured in derived plasma by Stago StaChrom/MLA Electra 900C.

Whole blood from a normal adult was drawn into a Vacutainer brand sample collection tube containing 0.105M (3.2%) sodium citrate at the ratio of 9 parts blood to 1 part citrate. After mixing the tube by gentle inversion, the citrated whole blood was aliquoted into plastic tubes and supplemented with the low molecular weight heparin (LMWH), Lovenox® (enoxaparin sodium) to yield five whole blood enoxaparin solutions with nominal concentrations ranging from about 0.0 to about 3.0 IU/ml enoxaparin. Each sample was tested once on a dry-chemistry LMWH test. The whole blood solutions were centrifuged within 5 minutes to obtain platelet poor plasma. The platelet poor plasma was then tested for enoxaparin concentration using the chromogenic STACHROM® LMWH assay (catalog #00906; Parsippany, N.J.), performed on an Electra 900C analyzer (Medical Laboratory Automation, Inc., Pleasantville, N.Y.). The results were calibrated to a preparation of enoxaparin (Aventis L/N WSD3075). This procedure was repeated for a total of ten normal adults. Individual results and the average for all 10 individuals is shown in Table 2 and FIG. 2.

These results show an increasing clotting time to increasing concentrations of enoxaparin and good correlation to the laboratory reference test.

The mean correlation (r) of the 10 individual dose-response relationship was 0.963.

Preferred Enoxaparin Embodiment

A small clinical trial was conducted at four centers with consenting patients primarily receiving enoxaparin for treatment of acute coronary syndromes and/or percutaneous coronary intervention (PCI) (n=35) and secondarily those receiving enoxaparin for prevention of deep venous thrombosis (DVT) during total knee/hip replacement (TKHR)(n=8). Two to four samples were collected from TKHR patients receiving subcutaneous (30 mg-BID SC) dosing with enoxaparin. Samples were collected to reflect peak anti-Xa activity (3–5 hours after dose) and at the nadir just prior to dosing) to obtain samples that span the entire range of anti-Xa activity. At least 3 samples were collected in patients undergoing PCI. PCI patients received drug via intravenous (IV) bolus (0.75 mg/kg) at the start of the procedure (D. J. Kereiakes et al., Combination enoxaparin and abciximab therapy during percutaneous coronary intervention: "NICE guys finish first". J Invasive Cardiol February; 12 Suppl A:1A–5A, (2000)). Samples were collected pre-drug administration (baseline), peak (5–15 minutes after bolus), therapeutic range (45–60 minutes after bolus), and then just prior to pulling the sheath (approx. 8–10 hours after bolus). Patients receiving UFH, direct thrombin inhibitors, and vitamin K antagonists were not eligible for this study. Batch anti-Xa determinations were performed using the STACHROM® LMWH assay (Diagnostica Stago, Parsippany, N.J.) on an Electra 900C analyzer (Medical Laboratory

TABLE 2

In Vitro Response of the Low Molecular Weight Heparin (LMWH) Test to enoxaparin in Whole Blood

| | | | | | | | R (correlation) |
|---|---|---|---|---|---|---|---|
| | Enoxaparin concentration* | 0.00 | 0.32 | 0.76 | 2.29 | 2.98 | |
| Donor 1 | LMWH Test Clotting Time (seconds) | 142.7 | 222.1 | 253.0 | 312.3 | 444.8 | 0.951 |
| | Enoxaparin concentration* | 0.00 | 0.37 | 0.78 | 1.94 | 2.75 | |
| Donor 2 | LMWH Test Clotting Time (seconds) | 127.6 | 193.8 | 259.6 | 346.8 | 405.2 | 0.981 |
| | Enoxaparin concentration* | 0.00 | 0.33 | 0.75 | 1.67 | 3.29 | |
| Donor 3 | LMWH Test Clotting Time (seconds) | 147.7 | 259.1 | 314.8 | 396.0 | 420.1 | 0.872 |
| | Enoxaparin concentration* | 0.00 | 0.35 | 0.75 | 1.67 | 2.32 | |
| Donor 4 | LMWH Test Clotting Time (seconds) | 104.8 | 196.8 | 260.5 | 309.6 | 351.0 | 0.944 |
| | Enoxaparin concentration* | 0.00 | 0.41 | 0.81 | 1.64 | 2.70 | |
| Donor 5 | LMWH Test Clotting Time (seconds) | 139.0 | 214.8 | 270.1 | 316.6 | 422.8 | 0.983 |
| | Enoxaparin concentration* | 0.00 | 0.37 | 0.80 | 1.82 | 3.16 | |
| Donor 6 | LMWH Test Clotting Time (seconds) | 152.0 | 206.8 | 272.0 | 350.8 | 381.1 | 0.942 |
| | Enoxaparin concentration* | 0.00 | 0.46 | 0.88 | 2.18 | 3.30 | |
| Donor 7 | LMWH Test Clotting Time (seconds) | 101.2 | 192.0 | 238.2 | 290.8 | 337.2 | 0.938 |
| | Enoxaparin concentration* | 0.00 | 0.44 | 0.93 | 2.23 | 3.32 | |
| Donor 8 | LMWH Test Clotting Time (seconds) | 111.1 | 196.6 | 252.6 | 307.6 | 365.5 | 0.955 |
| | Enoxaparin concentration* | 0.00 | 0.37 | 0.87 | 1.82 | 2.96 | |
| Donor 9 | LMWH Test Clotting Time (seconds) | 101.2 | 177.8 | 236.1 | 297.8 | 348.9 | 0.958 |
| | Enoxaparin concentration* | 0.00 | 0.41 | 0.82 | 1.97 | 3.04 | |
| Donor 10 | rep1 | 101.0 | 171.3 | 210.8 | 278.2 | 330.5 | 0.972 |
| | Average Enoxaparin Concentration | 0.00 | 0.38 | 0.82 | 1.92 | 2.98 | |
| | Average LMWH Test Clotting Time (seconds) | 122.8 | 203.1 | 256.8 | 320.7 | 380.7 | 0.963 |
| | STDEV | 21.1 | 24.9 | 27.3 | 34.7 | 40.2 | |

Automation, Inc., Pleasantville, N.Y.) which measures anti-Xa activity using the amidolytic method. The results were calibrated to a standard preparation of enoxaparin (L/N WSD3075 Aventis Pharmaceuticals, Inc., Strasbourg 67917, France).

Samples were collected at four sites from 31 male and 12 female patients. Demographics, date of birth, sex, age, height, weight, and total body surface area (TBSA) of each patient are found in TABLE 3. The primary indication for hospitalization at Site 3 was for knee and hip replacement surgery while at the other sites the indication was for PCI. Treatment information at the four contributing sites is summarized in Table 4. The inclusion of IV administered enoxaparin achieved anti-Xa levels from 1–2 anti-Xa IU/ml in derived plasma. A total of 116 samples from 43 patients were included in this study.

Figure 5:
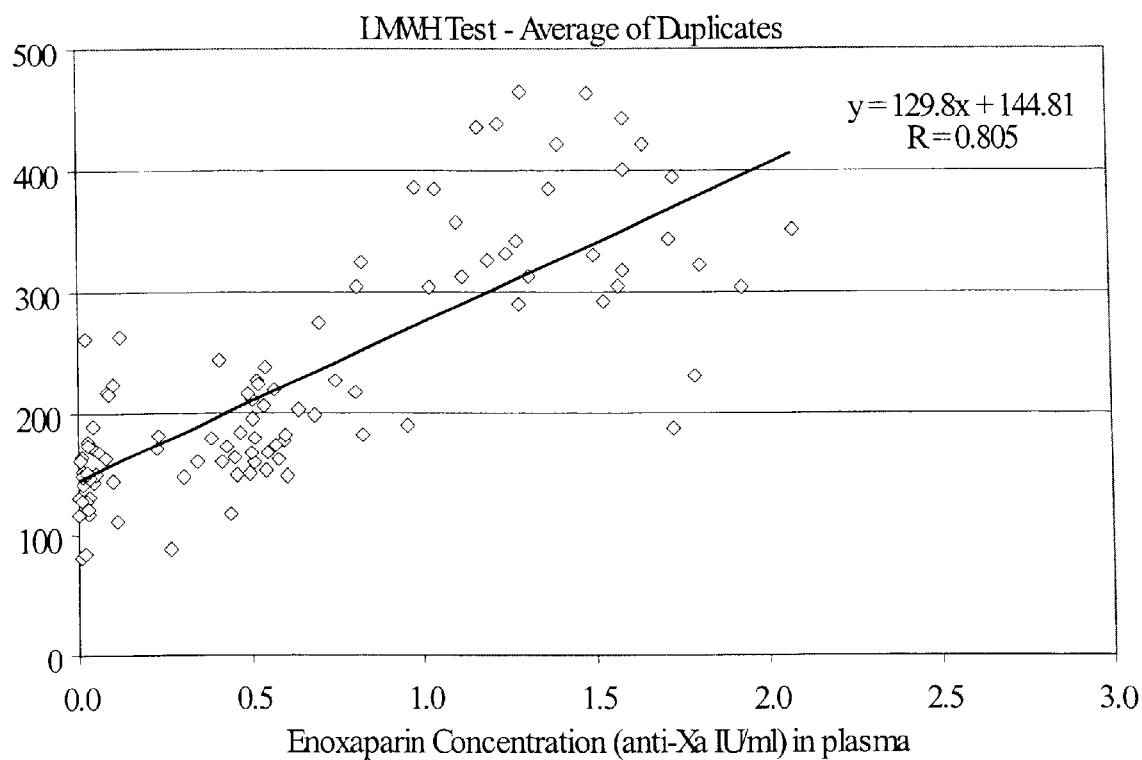
FIG. 5 shows the relationship between the ENOX test clot times for CWB and STACHROM® LMWH anti-Xa IU/ml values (from derived plasma) in a small clinical trial.

The relationship between the ENOX test clot times for CWB and STACHROM® LMWH anti-Xa IU/ml values (from derived plasma) are shown in FIG. 5. Correlation between the ENOX test card clot times and the STACHROM® LMWH results is shown with linear regression and has a correlation coefficient (r) of 0.805. A similar relationship between the ENOX test and the STACHROM® LMWH was observed if the results of individual clot time measurements were compared to the single STACHROM® LMWH anti-Xa IU/ml measurement (r=0.777). Overall, the trial provided an appropriate concentration range of enoxaparin containing samples for evaluation of the ENOX test card, especially for PCI patients in the range of 0.6 to 1.8 anti-Xa IU/ml of enoxaparin (J. P. Collet et al, Percutaneous coronary intervention after subcutaneous enoxaparin pretreatment in patients with unstable angina pectoris. Circulation February 6;103(5):658–63 (2001)).

TABLE 3

Demographics of the Enoxaparin Test Clinical Trial

| Site | Gender Female | Male | Total | | Age (Yrs) | Height (cm) | Weight (kg) | TBSA (m2) |
|---|---|---|---|---|---|---|---|---|
| 1 | 4 | 16 | 20 | Mean | 67.4 | 173.2 | 83.4 | 2.00 |
|   |   |   |   | Max  | 83   | 188.0 | 111.2 | 2.41 |
|   |   |   |   | Min  | 48   | 150.0 | 53.0  | 1.49 |
| 2 | 3 | 4  | 7  | Mean | 65   | 166.1 | 88.5  | 2.02 |
|   |   |   |   | Max  | 80   | 185.0 | 102.1 | 2.19 |
|   |   |   |   | Min  | 54   | 129.5 | 77.7  | 1.69 |
| 3 | 2 | 6  | 8  | Mean | 60.5 | 164.1 | 70.2  | 1.78 |
|   |   |   |   | Max  | 69   | 190.5 | 96.0  | 2.25 |
|   |   |   |   | Min  | 37   | 152.4 | 50.0  | 1.48 |
| 4 | 3 | 5  | 8  | Mean | 63.3 | 169.3 | 73.8  | 1.85 |
|   |   |   |   | Max  | 78   | 185.0 | 93.0  | 2.16 |
|   |   |   |   | Min  | 51   | 157.0 | 42.2  | 1.36 |
| All Sites | 12 | 31 | 43 | Mean | 64.9 | 169.6 | 80.0 | 1.93 |
|   |   |   |   | Max  | 83   | 190.5 | 111.2 | 2.41 |
|   |   |   |   | Min  | 37   | 129.5 | 42.2  | 1.36 |

TABLE 4

Dosing Regimes from Sites and Primary Indication

| Sites | Treatment | Primary Indication |
|---|---|---|
| 1 | 0.75 mg/kg IV | PCI/PTCA |
| 2 | 0.75 mg/kg IV | PCI |
| 3 | 30 mg qd SC | Orthopedic Surgery |
| 4 | 0.73 to 1.07 mg/kg IV | PCI |

Clotting times (CT) from citrated whole blood CWB samples ranged from 80 to 470 seconds as measured by the Rapidpoint® ENOX test. Fifty-one samples (44%) had CT of 199 seconds or less, 36 samples (31%) had a CT of 200 to 300 seconds, and 29 samples (25%) had a CT of greater than 300 seconds. The population coefficient of variation (CV) for duplicate clot time measurements was 8.8% in whole blood. These coefficients of variation are acceptable. Corresponding derived-plasma enoxaparin concentrations ranged from 0.0 to 1.8 anti-Xa IU/ml. Distribution of enoxaparin concentrations observed in the plasma derived from these clinical samples (n=116) was 41 samples (36%) <0.1 IU/ml, 49 samples (43%) 0.1 to 1.0 IU/ml, and 26 samples (22%) 1.1 to 1.8 IU/ml as measured by Stago Stachrom anti-Xa assay. The population coefficient of variation for the STACHROM® LMWH method using duplicate anti-Xa IU/ml measurements was 9.4%. This relatively high CV may be due to the additional error introduced by dilution of samples that contain enoxaparin concentrations beyond the range of the STACHROM® LMWH test (This range is 0.0–1.0 anti-Xa IU/ml).

Figure 4:
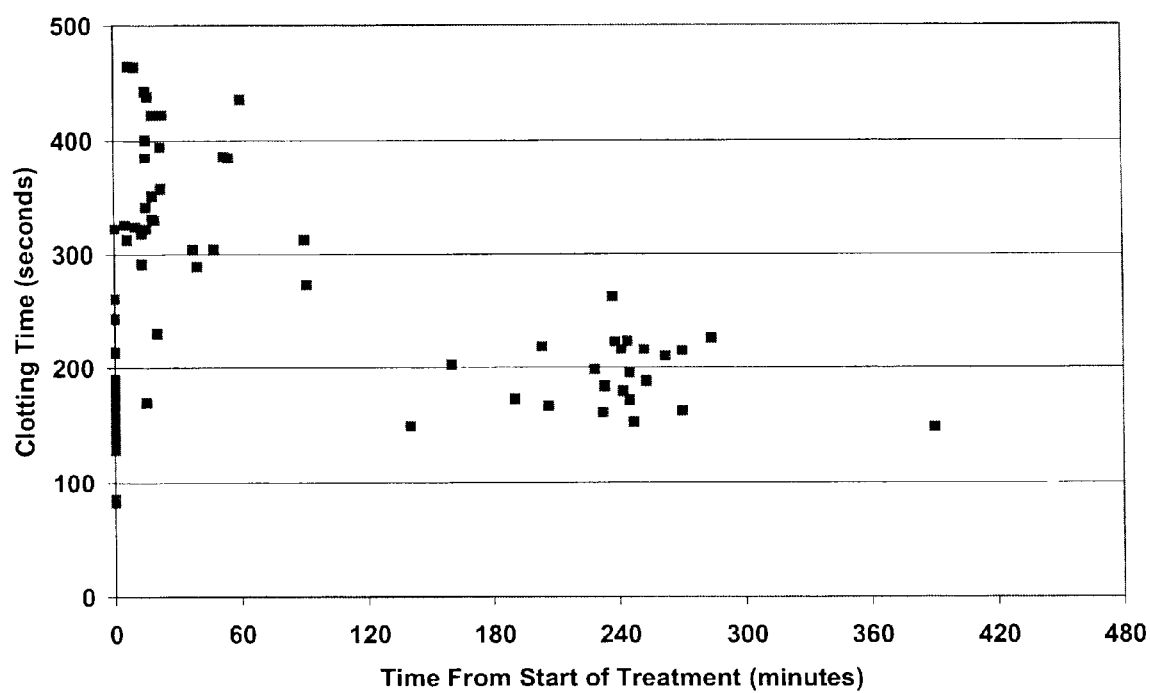
FIG. 4 shows the response of the preferred ENOX test and the corresponding derived plasma anti-Xa values as a function of time from enoxaparin administration.

FIG. 4 shows the response of the ENOX test and the corresponding derived plasma anti-Xa values as a function of time from enoxaparin administration. The two sets of data mirror each other with the peak in vivo enoxaparin concentration occurring within 10 minutes of injection and the ENOX test response also maximal at this time. These results indicate that the response of ENOX test follows the pharmacokinetics of enoxaparin.

Interference Studies

A. Deficient Plasma Studies

Figure 6:
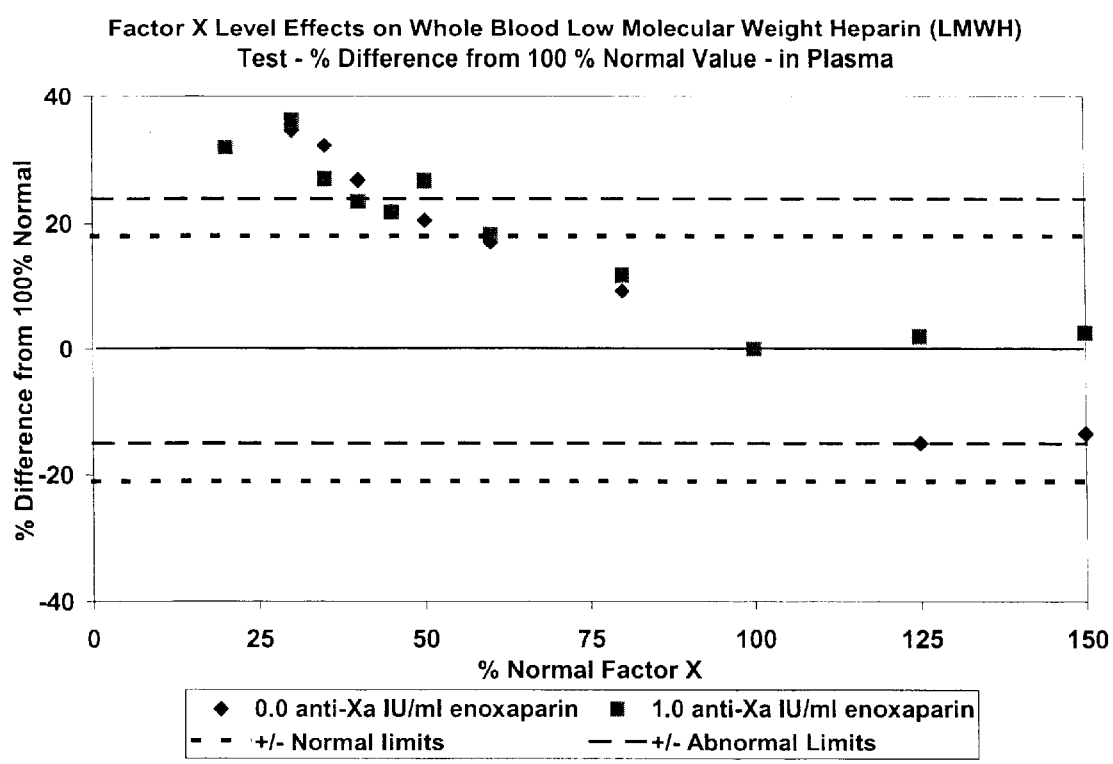
FIG. 6 shows the results of a study on depletion of various factors in blood samples on the ENOX test clot times.

In vitro studies were performed with normal pooled and affinity-depleted plasmas to determine the factor sensitivities of the test. At the plasma equivalent of 1.0 anti-Xa IU/ml enoxaparin clotting time increased 20% or more when levels of fibrinogen, prothrombin, and Factor X decreased to levels of <10%, <10%, and 60% of normal, respectively. A representative summary of the studies for Factor X is shown in FIG. 6. A decrease in antithrombin of 90% of normal led to a decrease in clotting time of 25%. The ENOX test is dependent upon these critical coagulation factors in the common cascade.

B. Drug Effects and Common Interferences

In vitro experiments using citrated whole blood indicates the ENOX test is insensitive to lipids (to 20 mg/ml), antiplatelet agents (abciximab, eptifibatide, tirofiban, aspirin) and fibrinolytic agents (alteplase, tenecteplase), and hematocrit. Hemodilution with IsoLyte or saline to 15% did not affect test results, Table 5.

TABLE 5

Summary of Interference Testing For Rapidpoint ® ENOX Test

| Interferent Tested | EFFECT | Sample Type |
|---|---|---|
| Lipid | No effect 0–20 mg/ml | CWB |
| Hematocrit | No effect 20–50% HCT | CWB |
| Hemodilution | No effect at 15% | CWB |
| Tirofiban | No effect at 0–5600 ng/ml | CWB |
| Aspirin | No effect at 0–300 ug/ml | CWB |
| Abciximab | No effect at 0–3600 ng/ml | CWB |
| Eptifibatide | No effect at 0–2600 ng/ml | CWB |
| Ketorolac tromethamine | No effect at 0–12 ng/ml | CWB |
| Alteplase | No effect at 1000–3200 ng/ml | CWB |
| Tenecteplase | No effect at 0–10,000 ng/ml | CWB |
| Nitroglycerin | No effect at 0–1000 ng/ml | CWB |

Repeatability in Preparation of Assay and Performance of Assay

The within run CV values for 0.0 and 1.0 IU/ml enoxaparin samples were 6.3 and 5.5% and the lot-to-lot CV values for 0.0 and 1.0 IU/ml enoxaparin samples were 5.2 and 5.5%, respectively. Total imprecision at 1.0 IU/ml enoxaparin was <7.0%.

It will be apparent from the above detailed description that there are many variations in the present invention and the same are deemed to be subject to this invention as set forth in the appended claims.

What is claimed is:

1. A method for measuring low molecular weight heparin concentration on a whole blood sample, comprising:
   (i) combining a first, whole blood, component of the assay with a second component of the assay to form a resulting mixture, wherein said second component comprises a dry coagulation assay reagent arranged in a substantially flattened configuration and containing magnetic particles distributed substantially homogeneously therethrough and comprising a factor Xa activator, and wherein said resulting mixture is subjected to (ia) an oscillating magnetic field or (ib) a moving permanent magnetic field or (ic) a combination of an oscillating magnetic field and a stationary permanent magnetic field or (id) a rotating magnetic field, whereby said combining of said first component with said second component substantially simultaneously initiates movement of said magnetic particles and a coagulation assay measurement; and
   (ii) monitoring movement induced in said magnetic particles by (ia) or (ib) or (ic) or (id) to obtain said coagulation assay measurement,
   wherein said coagulation assay measurement correlates to a concentration of low molecular weight heparin in the whole blood sample.

2. The method of claim 1, wherein said whole blood sample is a citrated whole blood sample.

3. The method of claim 1, wherein said magnetic particles are induced to move by applying an oscillating magnetic field thereto.

4. The method of claim 1, wherein said magnetic particles are induced to move by applying a moving permanent magnetic field thereto.

5. The method of claim 1, wherein said method is carried out in an element for performing said method, said method comprising adding said first, whole blood, component to said element, wherein said element comprises a channel structure defining a sample well and a reaction volume in fluid communication with each other, said reaction volume containing said second component, said channel structure having a geometry causing said first, whole blood, component placed in said sample well to be drawn into and filling said reaction volume via capillary action, wherein, after said reaction volume is filled, said first, whole blood, component remains stationary therein.

6. The method of claim 5, wherein said element further comprises a means for channeling light from an outside source to said reaction volume.

7. The method of claim 6, further comprising using a means for detecting light scattered or absorbed or reflected from said reaction volume.

8. The method of claim 7, wherein said element is disposed in sufficiently close proximity to a permanent magnet and to an electromagnet such that said permanent magnet and said electromagnet provide said combination of an oscillating magnetic field and a stationary permanent magnetic field.

9. The method of claim 8, wherein said element is situated between said permanent magnet and said electromagnet.

10. The method of claim 1, wherein said magnetic particles are induced to move by application of a rotating magnetic field.

11. The method of claim 1, wherein said Factor Xa activator is Russell's Viper Venom.

12. The method of claim 1, wherein said low molecular weight heparin is enoxaparin.

13. A method for measuring low molecular weight heparin concentration in a whole blood sample, comprising:
   (i) adding a whole blood sample to a sample well of an element comprising:
      a channel structure defining the sample well and a reaction volume in fluid communication with each other, wherein said reaction volume is defined by an upper surface having attached thereto a reflectance layer, comprising a semipermeable matrix wherein said reaction volume contains a measured amount of at least one dry coagulation assay reagent arranged in a substantially flattened configuration and containing magnetic particles distributed substantially homogeneously therethrough, wherein a specific volume of said sample is drawn into said reaction volume by capillary action and contacts, together with said semipermeable layer, said reagent to thereby substantially simultaneously initiate a coagulation assay measurement; and
   (ii) performing said coagulation assay measurement by measurement the reflectance of said semipermeable layer,
   wherein said dry coagulation assay reagent comprises a Factor Xa activator.

14. A kit for measuring low molecular weight heparin concentration on a whole blood sample, comprising, in one or more containers, a permanent magnet, a timing means, and an element containing at least one dry coagulation assay reagent arranged in a substantially flattened format and containing magnetic particles distributed substantially homogeneously therethrough, wherein said at least one dry coagulation assay reagent comprises a Factor Xa activator.

15. The kit of claim 14, further comprising a transfer pipette.

16. The kit of claim 15, wherein said transfer pipette is made of an essentially nonthrombogenic material, comprises a vented end, is capable of being filled with a liquid sample by capillary action, and is capable of expelling said liquid sample by means of pressure after covering or sealing said vented end.

17. A system for measuring low molecular weight heparin concentration in a whole blood sample, comprising:
   (i) an instrument with a means for temperature control, a means for producing an oscillating magnetic field or for moving a permanent magnetic field, an illuminating means, and a photometric monitoring means; and (ii) an element for performing said measuring, said element comprising a channel structure defining a sample well and reaction volume in fluid communication with each other, said channel structure having a geometry causing a liquid sample placed in said sample well to be drawn into and filling said reaction volume via capillary action, said reaction volume comprising at least one dry coagulation assay reagent arranged in a substantially flattened configuration and containing magnetic particles distributed substantially homogeneously therethrough, wherein said at least one dry coagulation assay reagent comprises a Factor Xa activator.

18. The system of claim 17, further comprising a transfer pipette.

19. The system of claim 18, wherein said transfer pipette is made of an essentially nonthrombogenic material, comprises a vented end, is capable of being filled with a liquid sample by capillary action, and is capable of expelling said liquid sample by means of pressure after covering or sealing said vented end.

20. The system of claim 17, wherein said instrument further comprises a heating means comprising a resistive heater strip and a thermistor situated in close proximity to said element.

21. The system of claim 17, wherein said element is suitable for performing a whole blood coagulation assay, said channel structure having a geometry causing a blood sample placed in said sample well to be drawn into and filling said reaction volume via capillary action, wherein after said reaction volume is filled, said blood sample remains stationary therein, and wherein said element further comprises an optically or magnetically encodable information means, or both, capable of providing at least one of calibration, quality control, test parameter and patient information.

22. The system of claim 17, wherein said illuminating means includes one or more light sources to illuminate said element and wherein said photometric monitoring means comprises one or more detectors for photometrically monitoring chromogenic or chromomodulating species present in said reaction volume.

23. A system for measuring low molecular weight heparin concentration in a whole blood sample, comprising:

(i) a reaction element comprising (1) a sample well for receiving a liquid sample and (2) a reaction chamber containing a dry coagulation assay reagent arranged in a substantially flattened configuration and in which is embedded, substantially homogeneously therethrough, magnetic particles;

(ii) said sample well and said reaction chamber being in fluid communication through a transport zone of geometry such that a volume of liquid sample placed in said sample well and corresponding to the volume of said reaction chamber is transported from said sample well to said reaction chamber simultaneously;

(iii) means for optically monitoring said reaction chamber;

(iv) means for subjecting said reaction chamber to an oscillating magnetic field;

(v) whereby, when said sample is introduced into said reaction chamber, said dry coagulation assay reagent is solubilized and said magnetic particles are thereby freed to move in an oscillating pattern induced by said oscillating magnetic field, thus providing a measurement of the kinetics of said coagulation assay corresponding to changes in the degree of said magnetic particles movement relative to said oscillating magnetic field, wherein said dry coagulation assay reagent comprises a Factor Xa activator.

24. The system of claim 23, further comprising a means for controlling the moment transport of said liquid sample from said sample well to said reaction chamber is initiated.

25. The system of claim 23, further comprising a plurality of reaction chambers in fluid communication with said sample well, and means for transporting a whole blood or plasma sample from one of said plurality of reaction chambers to another of said plurality of reaction chambers.

26. A method for measuring low molecular weight heparin concentration in a whole blood sample, comprising:

(i) subjecting to an oscillating magnetic field a reaction element bearing (1) a sample well for receiving a whole blood sample and (2) a reaction chamber containing a dry coagulation assay reagent arranged in a substantially flattened format and in which is embedded, substantially homogeneously therethrough, magnetic particles, said sample well and reaction chamber being in fluid communication through a transport zone of geometry such that a volume of sample placed in said sample well and corresponding to the volume of said reaction chamber is transported from said sample well to said reaction chamber simultaneously;

(ii) adding the whole blood sample susceptible to coagulation to said sample well whereby at least a part of said sample is introduced simultaneously to said reaction chamber, said reagent is solubilized and said particles are freed to move in an oscillating pattern induced by said oscillating magnetic field; and (iii) optically monitoring said reaction chamber to measure kinetics for the coagulation assay corresponding to changes in the degree of said particle movement relative to said magnetic field, wherein said dry coagulation assay reagent comprises a Factor Xa activator.

* * * * *